United States Patent
Yokozeki

(10) Patent No.: US 6,602,198 B2
(45) Date of Patent: Aug. 5, 2003

(54) AUTOMATIC BLOOD-PRESSURE MEASURING APPARATUS

(75) Inventor: Akihiro Yokozeki, Komaki (JP)

(73) Assignee: Colin Corporation, Komaki (JP)

( * ) Notice: Subject to any disclaimer, the term of this patent is extended or adjusted under 35 U.S.C. 154(b) by 0 days.

(21) Appl. No.: 09/964,574

(22) Filed: Sep. 28, 2001

(65) Prior Publication Data

US 2002/0052554 A1 May 2, 2002

(30) Foreign Application Priority Data

Oct. 30, 2000 (JP) ........................................ 2000-330594

(51) Int. Cl.[7] ................................................ A61B 5/02
(52) U.S. Cl. ...................................... 600/485; 600/500
(58) Field of Search .................................. 600/485–504

(56) References Cited

U.S. PATENT DOCUMENTS

| | | | | |
|---|---|---|---|---|
| 5,165,416 A | * | 11/1992 | Shinoda et al. | 600/485 |
| 5,255,686 A | * | 10/1993 | Takeda et al. | 600/494 |
| 5,522,395 A | * | 6/1996 | Shirasaki et al. | 600/495 |
| 5,961,467 A | * | 10/1999 | Shimazu et al. | 600/485 |

FOREIGN PATENT DOCUMENTS

| | | |
|---|---|---|
| JP | A-8-187227 | 7/1996 |
| JP | A-9-253059 | 9/1997 |
| JP | B2-2938234 | 6/1999 |
| JP | B2-2975753 | 9/1999 |

* cited by examiner

Primary Examiner—Robert L. Nasser
Assistant Examiner—Patricia Mallari
(74) Attorney, Agent, or Firm—Oliff & Berridge, PLC

(57) ABSTRACT

An apparatus for automatically measuring a blood pressure of a living subject, including an inflatable cuff which is wound around a portion of the subject, a cuff pulse wave including heartbeat-synchronous pulses occurring to the cuff when a pressure in the cuff is changed, a pressure-pulse-wave detecting device which includes a pressure-pulse-wave sensor that is pressed against an artery of the subject and which detects, through the sensor, a pressure pulse wave that is produced by the artery when the pressure of the cuff is changed and that includes heartbeat-synchronous pulses, a correction-factor determining device for determining, for each of the heartbeat-synchronous pulses of the pressure pulse wave, a correction factor to correct an amplitude of each heartbeat-synchronous pulse to a predetermined value, a corrected-cuff-pulse-wave-amplitude determining device for multiplying, by the correction factor determined for each of the heartbeat-synchronous pulses of the pressure pulse wave, an amplitude of one of the heartbeat-synchronous pulses of the cuff pulse wave that corresponds to each heartbeat-synchronous pulse of the pressure pulse wave, and thereby determining a corrected amplitude of the one heartbeat-synchronous pulse of the cuff pulse wave, and a blood-pressure determining device for determining a blood pressure of the subject based on a change of the respective corrected amplitudes of the respective pulses of the cuff pulse wave, with respect to the pressure of the cuff.

7 Claims, 11 Drawing Sheets

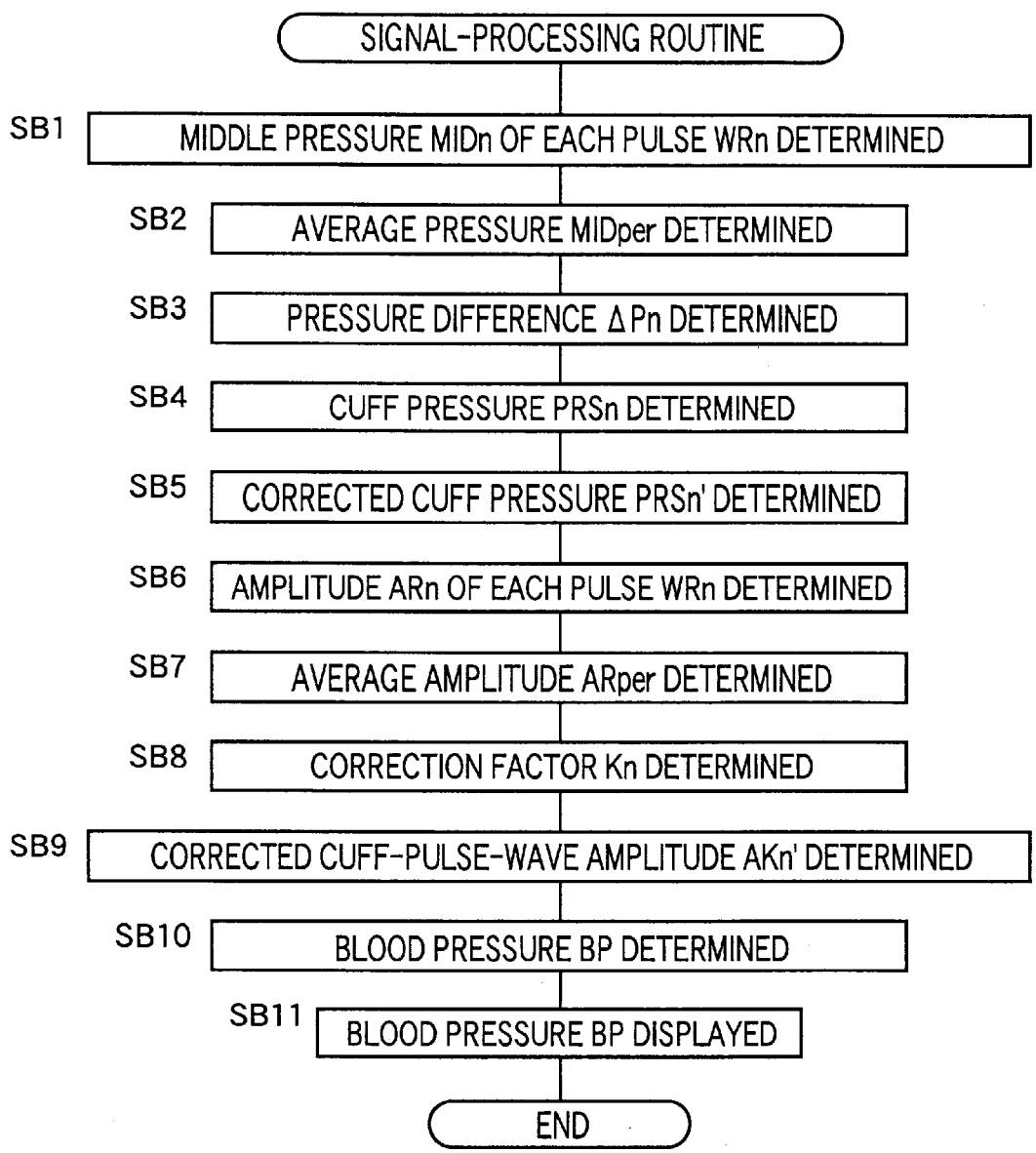

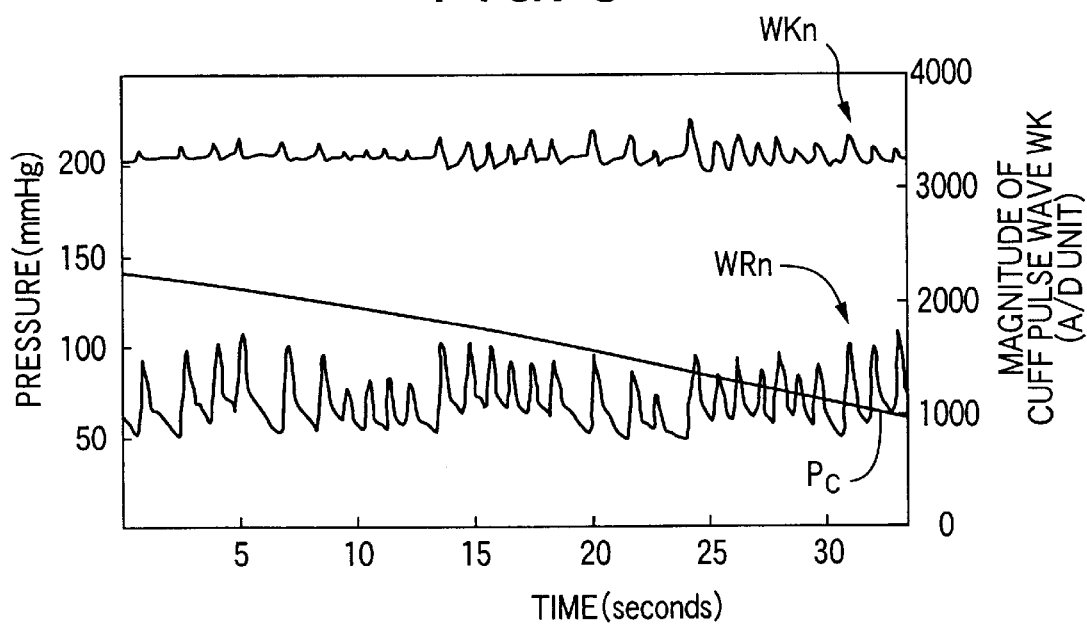

AUTOMATIC BLOOD-PRESSURE MEASURING APPARATUS

BACKGROUND OF THE INVENTION

1. Field of the Invention

The present invention relates to an apparatus for automatically measuring a blood pressure of a living subject according to so-called oscillometric method.

2. Related Art Statement

The oscillometric blood-pressure measuring method is carried out as follows: A pressing pressure of an inflatable cuff which is wound around, e.g., an upper arm of a living subject, that is, a cuff pressure is slowly changed, and a blood pressure of the subject is determined based on the change of an oscillatory component occurring to the cuff during the changing of the cuff pressure, that is, respective amplitudes of respective heartbeat-synchronous pulses of a cuff pulse wave with respect to the cuff pressure. An automatic blood-pressure measuring apparatus which employs the oscillometric method can measure a blood pressure at a front neck, a finger, or an inferior limb of a living subject where it is difficult to measure a blood pressure according to a microphone-using method. In addition, the microphone-using method requires a microphone to be accurately positioned on an artery of a subject, whereas the oscillometric method just needs a cuff to be wound around a portion of a subject. Thus, the oscillometric method can be easily carried out by both skilled and non-skilled operators. Moreover, the oscillometric method can be carried out at a noisy place, or on a child or an in-shock patient who produces small Korotkoff sounds only. Thus, the oscillometric-type automatic blood-pressure measuring devices have come into wide use.

However, according to the oscillometric method, a blood pressure is determined based on the change of respective amplitudes of respective pulses of the cuff pulse wave occurring to the cuff during a certain measurement-time duration, on the assumption that the blood pressure of the subject does not change during that time duration. If the blood pressure of the subject largely changes during the time duration, the envelope of the respective amplitudes largely deforms, which leads to determining an inaccurate blood pressure or even failing to determine a blood pressure.

SUMMARY OF THE INVENTION

It is therefore an object of the present invention to provide an apparatus which automatically measures a blood pressure of a living subject with a high accuracy.

The above object has been achieved by the present invention. According to a first feature of the present invention, there is provided an apparatus for automatically measuring a blood pressure of a living subject, comprising an inflatable cuff which is adapted to be wound around a portion of the subject, a cuff pulse wave including a plurality of heartbeat-synchronous pulses occurring to the cuff when a pressure in the cuff is changed; a pressure-pulse-wave detecting device which includes a pressure-pulse-wave sensor that is adapted to be pressed against an artery of the subject and which detects, through the pressure-pulse-wave sensor, a pressure pulse wave that is produced by the artery when the pressure of the cuff is changed and that includes a plurality of heartbeat-synchronous pulses; a correction-factor determining means for determining, for each of the heartbeat-synchronous pulses of the pressure pulse wave, a correction factor to correct an amplitude of the each heartbeat-synchronous pulse to a predetermined value; a corrected-cuff-pulse-wave-amplitude determining means for multiplying, by the correction factor determined by the correction-factor determining means for the each of the heartbeat-synchronous pulses of the pressure pulse wave, an amplitude of one of the heartbeat-synchronous pulses of the cuff pulse wave that corresponds to the each heartbeat-synchronous pulse of the pressure pulse wave, and thereby determining a corrected amplitude of the one heartbeat-synchronous pulse of the cuff pulse wave; and a blood-pressure determining means for determining a blood pressure of the subject based on a change of the respective corrected amplitudes of the respective heartbeat-synchronous pulses of the cuff pulse wave, with respect to the pressure of the cuff.

According to this feature, the correction-factor determining means determines, for each of the heartbeat-synchronous pulses of the pressure pulse wave detected by the pressure-pulse-wave detecting device, a correction factor to correct an amplitude of the each heartbeat-synchronous pulse to a predetermined value, and the corrected-cuff-pulse-wave-amplitude determining means multiplies, by the correction factor determined by the correction-factor determining means for the each of the heartbeat-synchronous pulses of the pressure pulse wave, an amplitude of one of the heartbeat-synchronous pulses of the cuff pulse wave that corresponds to the each heartbeat-synchronous pulse of the pressure pulse wave, and thereby determines a corrected amplitude of the one heartbeat-synchronous pulse of the cuff pulse wave. The respective corrected amplitudes of the heartbeat-synchronous pulses of the cuff pulse wave are freed of the influence of change of cardiac output during the change of the cuff pressure. Since the blood-pressure determining means determines a blood pressure of the subject based on a change of the respective corrected amplitudes of the heartbeat-synchronous pulses of the cuff pulse wave, with respect to the cuff pressure, the determined blood pressure enjoys a high accuracy.

According to a second feature of the present invention, there is provided an apparatus for automatically measuring a blood pressure of a living subject, comprising an inflatable cuff which is adapted to be wound around a portion of the subject, a cuff pulse wave including a plurality of heartbeat-synchronous pulses occurring to the cuff when a pressure in the cuff is changed; a pressure-pulse-wave detecting device which includes a pressure-pulse-wave sensor that is adapted to be pressed against an artery of the subject and which detects, through the pressure-pulse-wave sensor, a pressure pulse wave that is produced by the artery when the pressure of the cuff is changed and that includes a plurality of heartbeat-synchronous pulses; an average-pressure determining means for determining an average pressure of respective reference pressures of the heartbeat-synchronous pulses of the pressure pulse wave that are detected by the pressure-pulse-wave detecting device when the pressure of the cuff is changed; a corrected-cuff-pressure determining means for subtracting, from a pressure of the cuff at a time of detection of one of the heartbeat-synchronous pulses of the cuff pulse wave that corresponds to each of the heartbeat-synchronous pulses of the pressure pulse wave, a pressure difference obtained by subtracting, from the reference pressure of the each heartbeat-synchronous pulse of the pressure pulse wave, the average pressure determined by the average-pressure determining means, and thereby determining a corrected pressure of the cuff, and a blood-pressure determining means for determining a blood pressure of the subject based on a change of respective amplitudes of the respective heartbeat-synchronous pulses of the cuff pulse wave, with respect to the respective corrected pressures of the cuff.

According to this feature, the average-pressure determining means determines the average pressure of the respective reference pressures of the heartbeat-synchronous pulses of the pressure pulse wave that are detected by the pressure-pulse-wave detecting device when the pressure of the cuff is changed, and the corrected-cuff-pressure determining means subtracts, from the pressure of the cuff at the time of detection of one of the heartbeat-synchronous pulses of the cuff pulse wave that corresponds to each of the heartbeat-synchronous pulses of the pressure pulse wave, the pressure difference obtained by subtracting, from the reference pressure of the each heartbeat-synchronous pulse of the pressure pulse wave, the average pressure determined by the average-pressure determining means, and thereby determines a corrected pressure of the cuff. The respective corrected pressures of the cuff indicate respective cuff pressures which would be detected at respective times of detection of the respective amplitudes of the pulses of the cuff pulse wave, in a state in which there would be no influence of change of blood pressure during the change of the cuff pressure. Since the blood-pressure determining means determines a blood pressure of the subject based on a change of respective amplitudes of the heartbeat-synchronous pulses of the cuff pulse wave, with respect to the respective corrected cuff pressures determined by the corrected-cuff-pressure determining means, the determined blood pressure enjoys a high accuracy.

According to a third feature of the present invention, there is provided an apparatus for automatically measuring a blood pressure of a living subject, comprising an inflatable cuff which is adapted to be wound around a portion of the subject, a cuff pulse wave including a plurality of heartbeat-synchronous pulses occurring to the cuff when a pressure in the cuff is changed; a pressure-pulse-wave detecting device which includes a pressure-pulse-wave sensor that is adapted to be pressed against an artery of the subject and which detects, through the pressure-pulse-wave sensor, a pressure pulse wave that is produced by the artery when the pressure of the cuff is changed and that includes a plurality of heartbeat-synchronous pulses; a correction-factor determining means for determining, for each of the heartbeat-synchronous pulses of the pressure pulse wave, a correction factor to correct an amplitude of the each heartbeat-synchronous pulse to a predetermined value; a corrected-cuff-pulse-wave-amplitude determining means for multiplying, by the correction factor determined by the correction-factor determining means for the each of the heartbeat-synchronous pulses of the pressure pulse wave, an amplitude of one of the heartbeat-synchronous pulses of the cuff pulse wave that corresponds to the each heartbeat-synchronous pulse of the pressure pulse wave; an average-pressure determining means for determining an average pressure of respective reference pressures of the heartbeat-synchronous pulses of the pressure pulse wave that are detected by the pressure-pulse-wave detecting device when the pressure of the cuff is changed; a corrected-cuff-pressure determining means for subtracting, from a pressure of the cuff at a time of detection of the one of the heartbeat-synchronous pulses of the cuff pulse wave that corresponds to the each of the heartbeat-synchronous pulses of the pressure pulse wave, a pressure difference obtained by subtracting, from the reference pressure of the each heartbeat-synchronous pulse of the pressure pulse wave, the average pressure determined by the average-pressure determining means; and a blood-pressure determining means for determining a blood pressure of the subject based on a change of the respective corrected amplitudes of the respective heartbeat-synchronous pulses of the cuff pulse wave, with respect to the respective corrected pressures of the cuff.

The third feature includes the above-described first and second features. That is, the blood-pressure determining means determines a blood pressure of the subject based on a change of the corrected amplitudes of the pulses of the cuff pulse wave, with respect to the corrected pressures of the cuff. Since the corrected amplitudes of the pulses of the cuff pulse wave are freed of the influence of change of cardiac output during the change of the cuff pressure and the corrected pressures of the cuff are freed of the influence of change of blood pressure during the same time duration, the determined blood pressure enjoys a high accuracy.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which:

FIG. 7 is a flow chart representing a signal-processing routine according to which the control device shown in FIG. 1 processes the obtained signals and thereby determines the blood pressure;

FIG. 8 is a graph showing a cuff pulse wave $WK_n$ and a radial pulse wave $WR_n$ which are obtained, when a cuff pressure $P_C$ is slowly decreased, by the automatic blood-pressure measuring apparatus of FIG. 1 to measure a blood pressure of a patient who suffers arrhythmia;

DETAILED DESCRIPTION OF PREFERRED EMBODIMENTS

Figure 1:
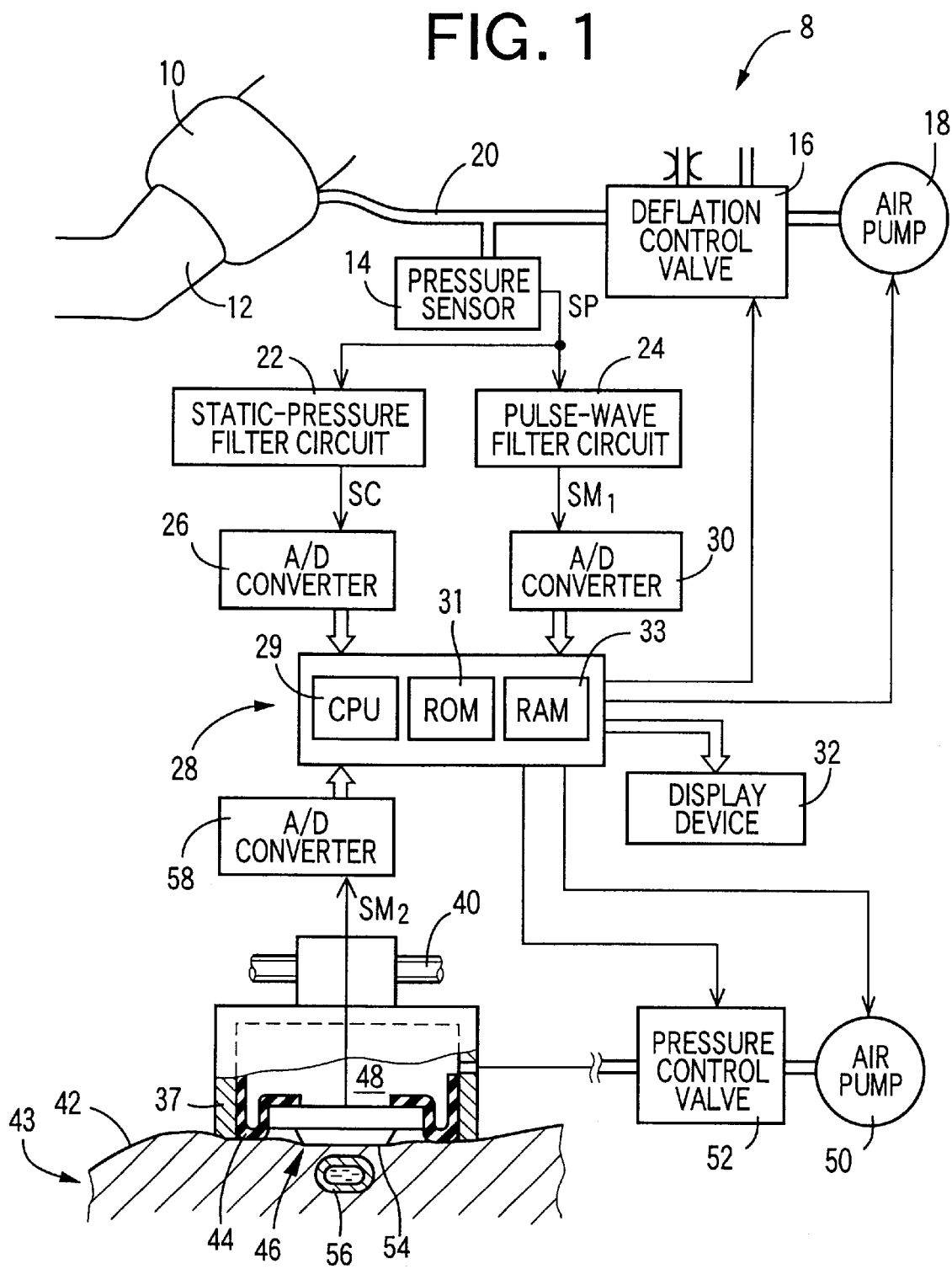
FIG. 1 is a diagrammatic view for explaining a construction of an automatic blood-pressure measuring apparatus to which the present invention is applied.

Hereinafter, there will be described an embodiment of the present invention in detail by reference to the accompanying drawings. FIG. 1 shows a diagrammatic view for explaining a construction of an automatic blood-pressure measuring apparatus 8 to which the present invention is applied.

In FIG. 1, reference numeral 10 designate an inflatable cuff which has a belt-like cloth bag and a rubber bag accommodated in the cloth bag and which is adapted to be wound around, e.g., a right upper arm 12 of a patient as a living subject. The cuff 10 is connected to a pressure sensor 14, a deflation control valve 16, and an air pump 18 via a piping 20. The deflation control valve 16 is selectively placed in a pressure-supply position in which the control valve 16 permits a pressurized air to be supplied from the air pump 18 to the cuff 10, a slow-deflation position in which the control valve 16 permits the pressurized air to be slowly discharged from the cuff 10, and a quick-deflation position in which the control valve 16 permits the pressurized air to be quickly discharged from the cuff 10.

The pressure sensor 14 detects an air pressure $P_C$ in the cuff 10, and supplies a pressure signal SP representing the detected pressure $P_C$, to each of a static-pressure filter circuit 22 and a pulse-wave filter circuit 24. The static-pressure filter circuit 22 includes a low-pass filter and extracts, from the pressure signal SP, a static-pressure component contained in the signal SP, i.e., a cuff-pressure signal SC representing the static pressure in the cuff 10. The cuff-pressure signal SC is supplied to a control device 28 via an analog-to-digital (A/D) converter 26. The pulse-wave filter circuit 24 includes a band-pass filter and extracts, from the pressure signal SP, an oscillating component having predetermined frequencies, i.e., a cuff-pulse-wave signal $SM_1$. The cuff-pulse-wave signal $SM_1$ is supplied to the control device 28 via an A/D converter 30. The cuff-pulse-wave signal $SM_1$ represents a cuff pulse wave $W_K$, i.e., a pressure pulse wave or an oscillatory pressure wave which is produced from a brachial artery, not shown, of the patient in synchronism with the heartbeat of the patient and is propagated to the cuff 10.

The control device 28 is provided by a so-called microcomputer including a central processing unit (CPU) 29, a read only memory (ROM) 31, a random access memory (RAM) 33 and an input-and-output (I/O) port, not shown. The CPU 29 processes signals according to the control programs pre-stored in the ROM 31 by utilizing the temporary-storage function of the RAM 33, and supplies drive signals via the I/O port to respective drive circuits, not shown, associated with the deflation control valve 16 and the air pump 18 so as to control the air pressure in the cuff 10 and perform an oscillometric blood-pressure measuring operation to measure a blood-pressure value BP of the patient, such as a systolic blood-pressure value $BP_{SYS}$ and/or a diastolic blood-pressure value $BP_{DIA}$. In addition, the CPU 29 operates a display device 32 to display the thus measured blood-pressure value BP. The display device 32 may have a cathode ray tube (CRT).

Figure 2:
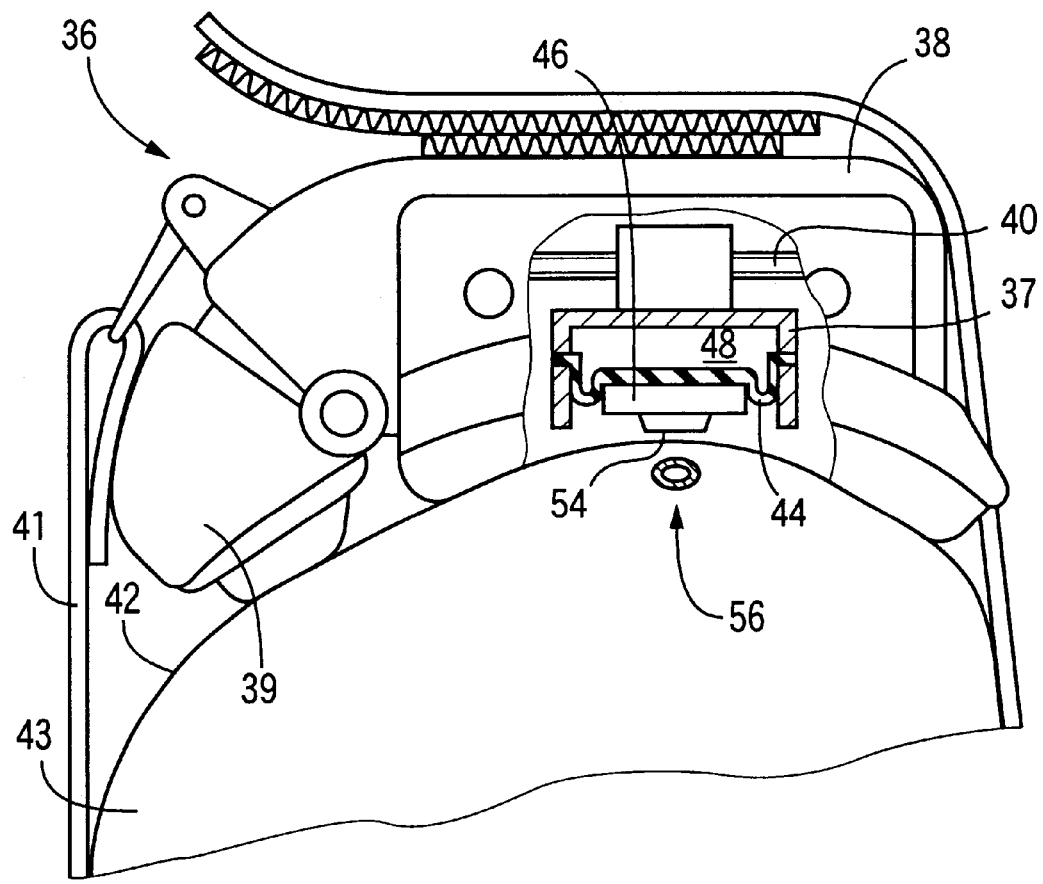
FIG. 2 is an enlarged view of a pressure-pulse-wave detecting probe of the apparatus of FIG. 1, a portion of the probe being cut away.

The monitoring apparatus 8 further includes a pressure-pulse-wave detecting probe 36 functioning as a pressure-pulse-wave detecting device. As shown in detail in FIG. 2, the pressure-pulse-wave detecting probe 36 includes a case 38 which accommodates a container-like sensor housing 37; and a feed screw 40 which is threadedly engaged with the sensor housing 37 and is rotated by an electric motor, not shown, provided in a drive section 39 of the case 38 so as to move the sensor housing 37 in a widthwise direction of a radial artery 56. With the help of a fastening band 41 which is connected to the case 38, the case 38 is detachably attached to a wrist 43 of the other arm than the arm wound which the cuff 10 is wound, such that an open end of the sensor housing 37 is opposed to a body surface 42 of the wrist. In addition, the probe 36 includes a pressure-pulse-wave sensor 46 which is secured via a diaphragm 44 to an inner wall of the sensor housing 37, such that the sensor 46 is movable relative to the housing 37 and is advanceable out of the open end of the same 37. The sensor housing 37, the diaphragm 44, etc. cooperate with one another to define a pressure chamber 48, which is supplied with a pressurized air from an air pump 50 via a pressure-control valve 52 so that the pressure-pulse-wave sensor 46 is pressed against the body surface 42 with a pressing force $P_{HDP}$ corresponding to the air pressure in the pressure chamber 48. Thus, the pressing force $P_{HDP}$ applied to the sensor 46 is expressed in terms of the air pressure (mmHg) in the pressure chamber 48.

The sensor housing 37 and the diaphragm 44 cooperate with each other to provide a pressing device 62 which presses the pressure-pulse-wave sensor 46 against the radial artery 56, with an optimum pressing force $P_{HDPO}$, described later. The feed screw 40 and the not-shown motor cooperate with each other to provide a pressing-position changing device or a widthwise-direction moving device 64 which moves the pressure-pulse-wave sensor 46 in the widthwise direction of the radial artery 56 and thereby changes a pressing position where the sensor 46 is pressed.

The pressure-pulse-wave sensor 46 includes a semiconductor chip provided by, e.g., a monocrystalline silicon, and having a flat press surface 54, and a number of semiconductor pressure-sensing elements (not shown) arranged on the press surface 154 at a regular interval of about 0.2 mm in the widthwise direction of the radial artery 56, i.e., the direction of movement of the sensor 46 parallel to the feed screw 40. The sensor 46 is pressed against the body surface 42 of the wrist 43 right above the radial artery 56, to detect a pressure pulse wave, i.e., an oscillatory pressure wave which is produced from the radial artery 56 and is propagated to the body surface 42, and supplies a pressure-pulse-wave signal $SM_2$ representing the pressure pulse wave, to the control device 28 via an A/D converter 58.

The CPU 29 of the control device 28 processes signals according to the control programs pre-stored in the ROM 31 by utilizing the temporary-storage function of the RAM 33, and supplies drive signals to respective drive circuits, not shown, associated with the pressure control valve 52 and the air pump 50 so as to control the air pressure in the pressure chamber 48. The control device 28 determines, based on the pressure pulse wave continuously detected by the pressure-pulse-wave sensor 46 while the pressure in the pressure chamber 48 is slowly changed, an optimum pressing pressure $P_{HDPO}$ at which the sensor 46 is pressed against the radial artery 56 such that a portion of the wall of the artery 56 is substantially flattened. The control device 28 controls the pressure control valve 52 so as to maintain the pressure of the pressure chamber 48 at the thus determined optimum pressing pressure $P_{HDP}$.

Figure 3:
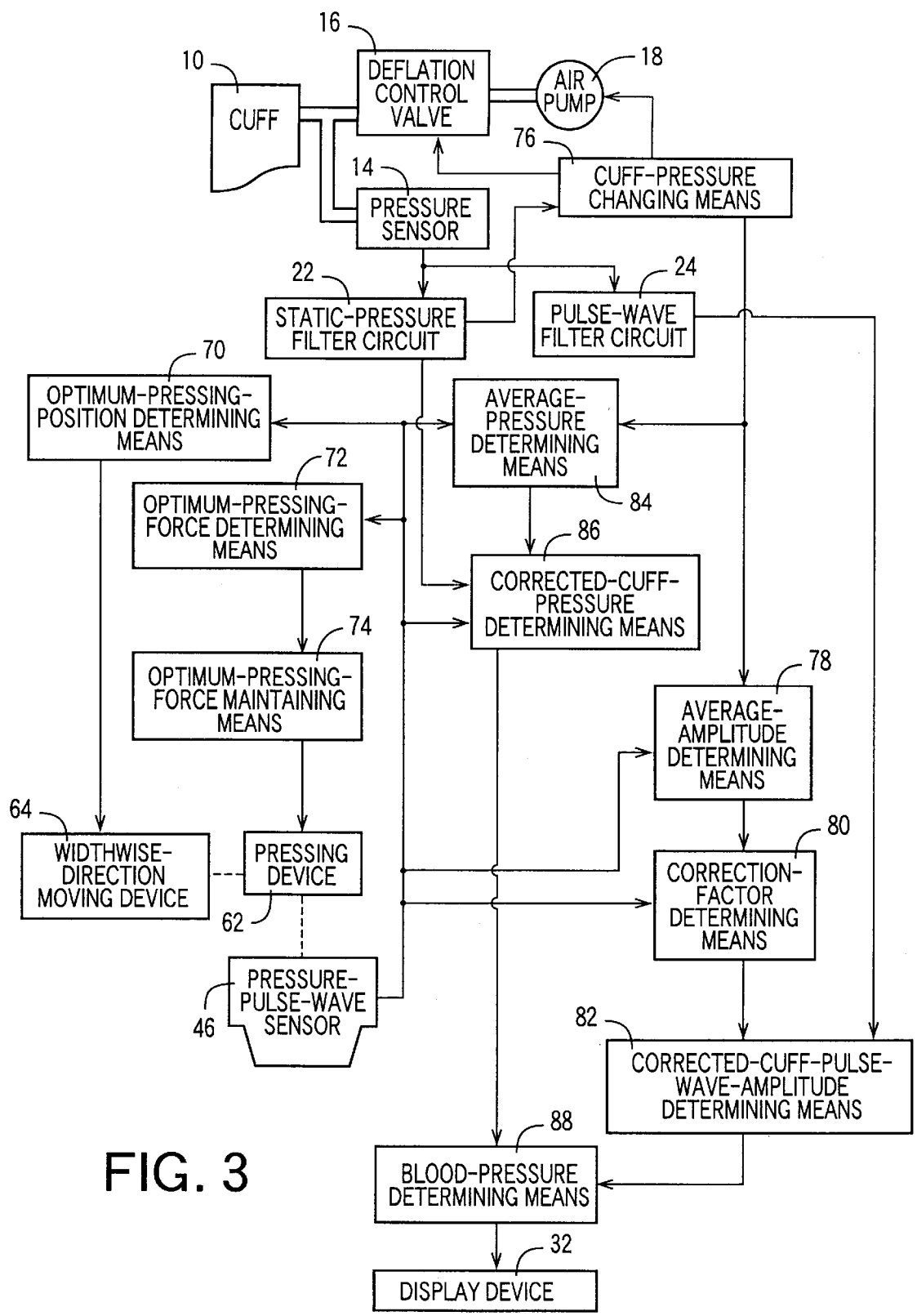
FIG. 3 is a block diagram for explaining essential functions of a control device of the apparatus of FIG. 1.

FIG. 3 is a block diagram for explaining essential functions of the control device 28. In the figure, an optimum-pressing-position determining means 70 operates when a prescribed pressing-position changing condition (i.e., an APS-starting condition) is satisfied, for example, when the pressure-pulse-wave detecting probe 36 is initially worn on the patient. The prescribed pressing-position changing condition may be defined such that the sensor 46 is largely moved relative to the radial artery 56 so that one of the pressure-sensing elements of the sensor 46 that detects the greatest one of the respective amplitudes of heartbeat-synchronous pulses detected by all the pressure-sensing elements is located in one of prescribed opposite end portions of the array of pressure-sensing elements. The determining means 70 operates the pressing device 62 to press the pressure-pulse-wave sensor 46 at a first prescribed pressing pressure P1 which would be sufficiently lower than an optimum pressing pressure $P_{HDPO}$ and, in this state, judges whether the one pressure-sensing element that detects the greatest amplitude is located in a prescribed middle portion of the array of pressure-sensing elements. If a negative judgment is made, that is, if the one pressure-sensing element that detects the greatest amplitude is not positioned in the prescribed middle portion, then the determining means 70 operates the pressing device 62 to move the sensor 46 away from the body surface 42 and operates the moving device 64, and again performs the above-described pressing and judging operations. Meanwhile, if a positive judgment is made indicating that the sensor 46 has been positioned at an optimum pressing position, the determining means 70 determines the pressure-sensing element detecting the greatest amplitude, as a middle pressure-sensing element (i.e., an active element), and stores data indicating the pressure-sensing element determined as the active element. Then, the determining means 70 allows an optimum-pressing-force determining means 72 to operate.

Figure 4:
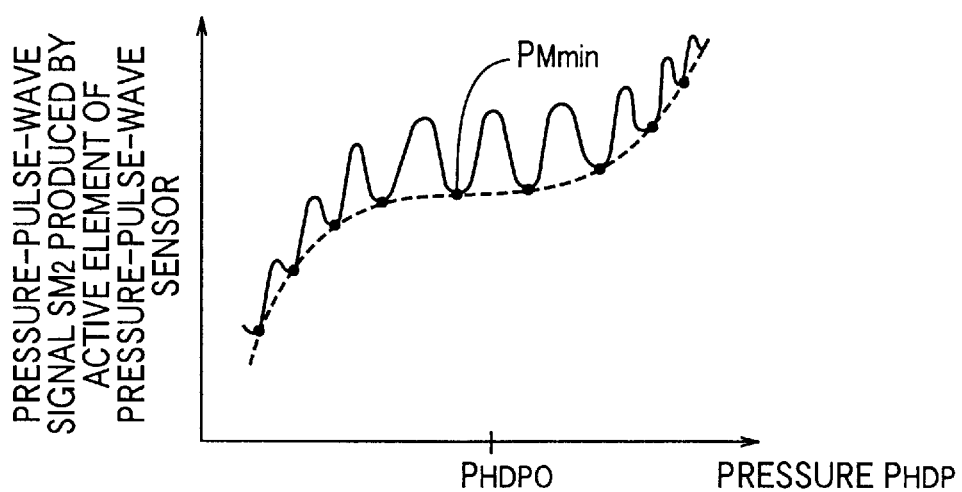
FIG. 4 is a graph for explaining a manner in which an optimum pressing force is determined by an optimum-pressing-force determining means shown in FIG. 3.

The optimum-pressing-force determining means 72 continuously changes the pressing pressure $P_{HDP}$ applied to the pressure-pulse-wave sensor 46 positioned at the optimum pressing position by the optimum-pressing-position determining means 70, and determines an optimum pressing pressure $P_{DHPO}$ based on the pressure pulse wave detected by the active element of the sensor 46. The optimum pressing pressure $P_{DHPO}$ may be determined as follows: First, as shown in a two-dimensional graph shown in FIG. 4, respective minimal values $P_{Mmin}$ of respective heartbeat-synchronous pulses of the pressure-pulse-wave signal $SM_2$ produced by the active element when the pressing pressure $P_{HDP}$ is continuously increased in a pressure range which would include the optimum pressing pressure $P_{DHPO}$, are determined, and then a curve (indicated at broken line in FIG. 4) connecting the respective minimal values $P_{Mmin}$ is determined. Further, the optimum pressing pressure $P_{DHPO}$ is determined as a pressure which falls within a pressure range which has a prescribed width and whose middle pressure is equal to a middle pressure of a pressure range in which the thus determined curve is substantially horizontal. If the radial artery 56 is pressed by the sensor 46 with the pressure falling within the latter pressure range, a portion of the wall of the artery 56 that is pressed by the sensor 46 is deformed to be substantially flat.

Figure 5:
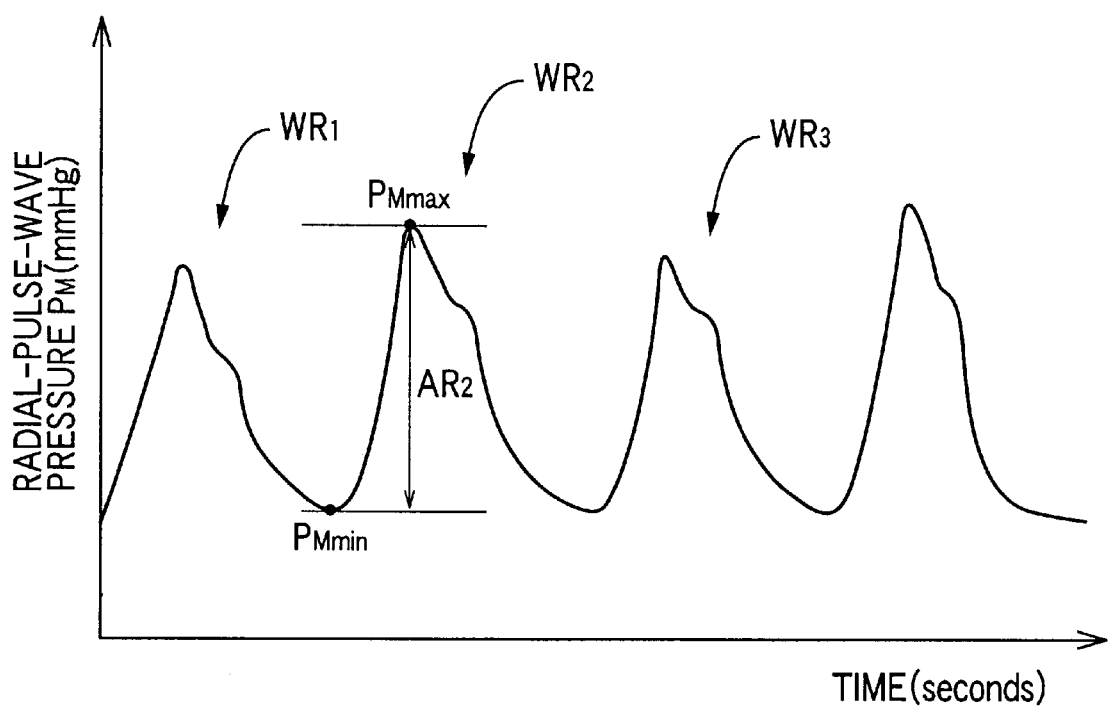
FIG. 5 is a graph showing respective heartbeat-synchronous pulses $WR_n$ (n=1, 2, 3, ...) of a pressure pulse wave that are continuously detected by a pressure-pulse-wave sensor.

An optimum-pressing-force maintaining means 74 operates the air pump 50 and the pressure control valve 52 to maintain the pressing pressure $P_{HDP}$ applied by the pressing device 62 to the pressure-pulse-wave sensor 46, at the optimum pressing pressure $P_{HDPO}$ determined by the optimum-pressing-force determining means 72. FIG. 5 shows respective heartbeat-synchronous pulses $WR_n$ (n=1, 2, 3, . . . ) of a pressure pulse wave (i.e., a radial pulse wave) which is continuously detected by the active element of the pressure-pulse-wave sensor 46 in the state in which the pressing pressure $P_{HDP}$ applied to the sensor 46 is maintained at the optimum pressing pressure $P_{HDPO}$.

A cuff-pressure changing means 76 operates, based on the cuff-pressure signal SC supplied from the static-pressure filter circuit 22, the air pump 18 and the deflation control valve 16 to quickly increase the pressing pressure of the cuff 10, i.e.,. the cuff pressure $P_C$ up to a prescribed first target pressure $P_{CM1}$ (e.g., 180 mmHg) which would be higher than a systolic blood-pressure value $BP_{SYS}$ of the patient and subsequently slowly decrease the cuff pressure $P_C$, at a rate of from 2 to 3 mmHg/sec, down to a prescribed second target pressure $P_{CM2}$ (e.g., 60 mmHg) which would be lower than a diastolic blood-pressure value $BP_{DIA}$ of the patient.

An average-amplitude determining means 78 determines respective amplitudes $AR_n$ of the respective heartbeat-synchronous pulses $WR_n$ of the pressure pulse wave which is detected by the active element of the pressure-pulse-wave sensor 46 while the cuff pressure $P_C$ is slowly decreased by the cuff-pressure changing means 76, and additionally determines an average $AR_{per}$ of the thus determined amplitudes $AR_n$. Here, as shown in FIG. 5, a pressure difference between a maximal pressure value $P_{Mmax}$ and a minimal pressure value $P_{Mmin}$ of each heartbeat-synchronous pulse $WR_n$ of the pressure pulse wave is defined as an amplitude $AR_n$ of the each pulse $WR_n$.

A correction-factor determining means 80 determines, for each heartbeat-synchronous pulse $WR_n$ of the pressure pulse wave detected by the pressure-pulse-wave 46, a correction factor $K_n$ as a ratio of the average amplitude $AR_{per}$ determined by the average-amplitude determining means 78, to the amplitude $AR_n$ of the each pulse $WR_n$, according to the following expression (1):

$$K_n = AR_{per}/AR_n \tag{1}$$

Since the average amplitude $AR_{per}$ is obtained by multiplying the amplitude $AR_n$ of the each pulse $WR_n$ by the correction factor $K_n$, the correction factor $K_n$ is a factor for correcting the amplitude $AR_n$ of the each pulse $WR_n$ to a predetermined value (i.e., the average amplitude $AR_{per}$).

A corrected-cuff-pulse-wave-amplitude determining means 82 multiplies an amplitude $AK_n$ of each of respective heartbeat-synchronous pulses $WK_n$ of the cuff pulse wave that respectively correspond to the respective heartbeat-synchronous pulses $WR_n$ of the pressure pulse wave, by the correction factor $K_n$ determined for a corresponding one of the pulses $WR_n$ by the correction-factor determining means 80, and thereby determines a corrected amplitude $AK_n'$ of the each heartbeat-synchronous pulse of the cuff pulse wave, according to the following expression (2):

$$AK_n' = AK_n X K_n \tag{2}$$

The each pulse $WK_n$ of the cuff pulse wave and the corresponding pulse $WR_n$ of the pressure pulse wave are produced by a same heartbeat of the patient. In the case where the cuff 10 is worn on the patient at the position which is more proximal to the heart of the patient than the position where the pressure-pulse-wave detecting probe 36 is worn, the each pulse $WK_n$ of the cuff pulse wave is followed by the corresponding pulse $WR_n$ of the pressure pulse wave.

As described above, the correction factor $K_n$ determined by the correction-factor determining means 80 is a factor for correcting the amplitude $AR_n$ of each pulse $WR_n$ of the pressure pulse wave to a predetermined value. That is, the correction factors $K_n$ are factors for removing respective fluctuations of the respective amplitudes $AR_n$ of the respective pulses $WR_n$ of the pressure pulse wave detected during the slow deflation of the cuff pressure $P_C$. It can be speculated that the same fluctuations of amplitudes would commonly occur to both the pressure pulse wave detected at the position where the pressure-pulse-wave probe 36 is worn and the cuff pulse wave detected at the position where the cuff 10 is worn. Therefore, the respective corrected amplitudes $AK_n'$ of the respective heartbeat-synchronous pulses $WK_n$ of the cuff pulse wave, obtained by multiplying the respective amplitudes $AK_n$ of the pulses $WK_n$ by the corresponding correction factors $K_n$, are free of the respective fluctuations of the amplitudes $AK_n$ of the pulses $WK_n$ detected during the slow deflation of the cuff pressure $P_C$.

An average-pressure determining means 84 determines an average $MID_{per}$ of respective middle pressures $MID_n$ of the respective heartbeat-synchronous pulses $WR_n$ of the pressure pulse wave continuously detected by the pressure-pulse-wave sensor 46 during the slow deflation of the cuff pressure $P_C$ by the cuff-pressure changing means 76. Here, an average of a maximal pressure value $P_{Mmax}$ and a minimal pressure value $P_{Mmin}$ of each pulse $WR_n$ of the pressure pulse wave is defined as a middle pressure $MID_n$ of the each pulse $WR_n$. The middle pressure $MID_n$ of the each pulse $WR_n$ provides a reference pressure of the each pulse $WR_n$.

A corrected-cuff-pressure determining means 86 determines, for each heartbeat-synchronous pulse $WR_n$ of the pressure pulse wave, a pressure difference $\Delta P_n$ (=$MID_n$−$MID_{per}$) by subtracting the average pressure $MID_{per}$ from the middle pressure of the each pulse $WR_n$. In addition, the determining means 86 determines a corrected cuff pressure $PRS_n'$ by subtracting the pressure difference $\Delta P_n$ determined for the each pulse $WR_n$, from a value $PRS_n$ of the cuff pressure $P_C$ at a time of detection of the amplitude $AK_n$ of one of the cuff pulses $WK_n$ that corresponds to the each pulse $WR_n$. The previously-explained definitions of the each pulse $WR_n$ and the corresponding pulse $WK_n$ used by the corrected-cuff-pulse-wave-amplitude determining means 82 applies to the corrected-cuff-pressure determining means 86.

Here, the meaning of the corrected cuff pressure obtained by subtracting, from the cuff-pressure value $PRS_n$ at the time of detection of the amplitude $AK_n$ of each pulse $WK_n$ of the cuff pulse wave, the middle pressure $MID_n$ of one pulse $WR_n$ of the pressure pulse wave that corresponds to the each pulse $WK_n$, can be expressed using the average pressure $MID_{per}$ as follows:

$$PRS_n - MID_n = PRS_n - MID_n + MID_{per} - MID_{per} \quad (3)$$

The right-hand side of the above expression (3) can be rewritten into the following expression (4) or (5):

$$(PRS_n - (MID_n - MID_{per})) - MID_{per} \quad (4)$$

$$(PRS_n - \Delta P_n) - MID_{per} \quad (5)$$

When the left-hand side of the expression (3) is compared with the expression (4) or (5), the middle pressure $MID_n$ corresponds to the average pressure $MID_{per}$, and the cuff pressure $PRS_n$ corresponds to the corrected cuff pressure ($PRS_n - \Delta P_n$). Therefore, if the amplitude $AK_n$ of the each cuff pulse observed at the middle pressure $MID_n$ and the cuff pressure $PRS_n$ is observed at the average pressure $MID_{per}$, then the cuff pressure should be the corrected cuff pressure ($PRS_n - \Delta P_n$). Thus, the corrected cuff pressure $PRS_n'$ is for correcting the cuff pressure $PRS_n$ at the time of detection of the amplitude $AK_n$ of the each cuff pulse $WK_n$, to a cuff pressure which is free of the influence of the fluctuation of the blood pressure (i.e., the fluctuation of the pressure pulse wave) of the patient during the slow deflation of the cuff pressure $P_C$. Thus, the pressure difference $\Delta P_n$ provides a correction value.

A blood-pressure determining means 88 determines a systolic blood-pressure value $BP_{SYS}$, a mean blood-pressure value $BP_{MEAN}$, and a diastolic blood-pressure value $BP_{DIA}$ of the patient, based on the change of the respective corrected cuff-pulse-wave amplitudes $AK_n'$ determined by the corrected-cuff-pulse-wave-amplitude determining means 82, with respect to the respective corrected cuff-pressure values $PRS_n'$ determined by the corrected-cuff-pressure determining means 86, according to an oscillometric blood-pressure determining algorithm. For example, the determining means 88 determines an envelope of the respective corrected cuff-pulse-wave amplitudes $AK_n'$, determines a cuff pressure $P_C$ corresponding to a rising point of the envelope as the systolic blood-pressure value $BP_{SYS}$, and determines a cuff pressure $P_C$ corresponding to a peak point of the envelope as the mean blood-pressure value $BP_{MEAN}$.

Figure 6:
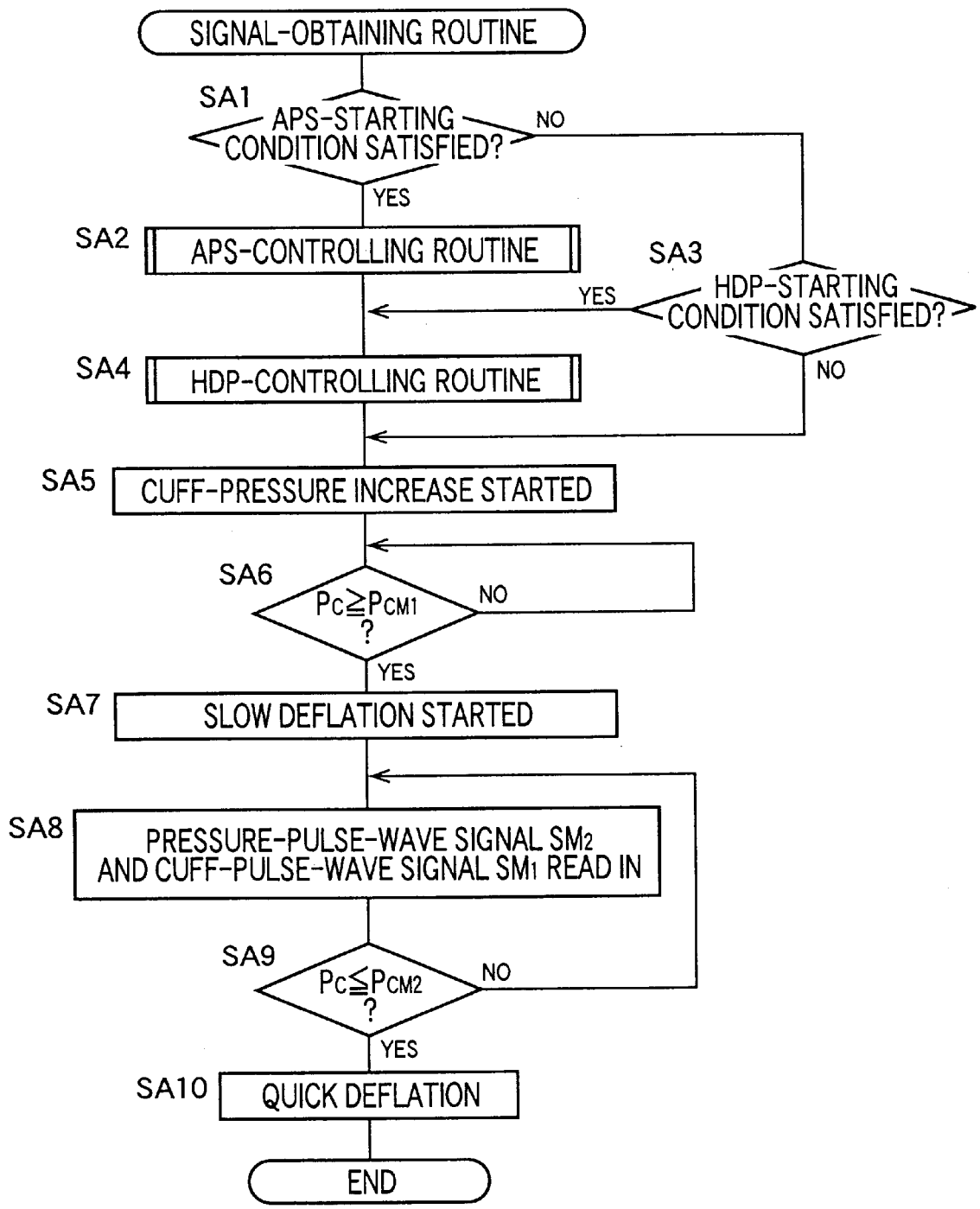
FIG. 6 is a flow chart representing a signal-obtaining routine according to which the control device shown in FIG. 1 obtains signals to determine a blood pressure of a patient.

FIGS. 6 and 7 are flow charts representing essential functions of the control device 28. FIG. 6 shows a signal-obtaining routine for obtaining signals to determine a blood pressure BP of a patient; and FIG. 7 shows a signal-processing routine for processing the signals obtained according to the signal-obtaining routine of FIG. 6 and thereby determining the blood pressure BP.

According to the signal-obtaining routine of FIG. 6, first, the control device 28 carries out Step SA1 (hereinafter, "Step" is omitted, if appropriate) and SA2 corresponding to the optimum-pressing-position determining means 70. At SA1, the control device 28 judges whether the prescribed pressing-position changing condition (i.e., the APS-starting condition) has been satisfied, for example, whether one of the pressure-sensing elements, arranged on the press surface 54 of the pressure-pulse-wave sensor 46, that detects the greatest one of the respective amplitudes of the respective pressure pulse waves detected by all the elements is located in either one of the opposite end portions of the array of elements.

If the pressing position where the pressure-pulse-wave sensor 46 is pressed against the radial artery 56 is not appropriate, for example, when the pressure-pulse-wave detecting probe 36 is initially worn on the patient, and accordingly if the prescribed pressing-position changing condition (the APS-starting condition) has been satisfied, a positive judgment is made at SA1, so that the control proceeds with SA2, i.e., an APS-controlling routine. According to this APS-controlling routine, the control device 28 determines an optimum pressing position where one of the pressure-sensing elements that is located at substantially the middle of the array of elements detects the greatest one of the respective amplitudes $AR_n$ of the respective pressure pulse waves detected by all the elements, that is, where one of the pressure-sensing elements that detects the greatest one of the respective amplitudes $AR_n$ of the respective pressure pulse waves detected by all the elements, is located at substantially the middle of the array of elements. In addition, the control device 28 determines, as an active element, the one pressure-sensing element located at substantially the middle of the array of elements.

On the other hand, if a negative judgment is made at SA1, the control goes to SA3 to judge whether a prescribed HDP-starting condition has been satisfied, indicating a need to update an optimum pressing force $P_{HDPO}$, for example, whether the greatest one of the respective amplitudes $AR_n$ of the respective pressure pulse waves $WR_n$ detected by the pressure-sensing elements of the pressure-pulse-wave sensor 46 is smaller than a prescribed standard value.

A negative judgment made at SA3 means that the pressure-pulse-wave sensor 46 is pressed at an appropriate pressing force or pressure $P_{HDP}$. Hence, the control goes to SA5 and the following steps, described later. On the other hand, when a positive judgment is made at SA3, or after the APS-controlling routine at SA2 has been carried out, the control goes to SA4, i.e., an HDP-controlling routine corresponding to the optimum-pressing-force determining means 72 and the optimum-pressing-force maintaining means 74. More specifically described, the control device 28 continuously increases the pressing force $P_{HDP}$ applied to the pressure-pulse-wave sensor 46, and determines, as an optimum pressing force $P_{HDPO}$, a value of the pressing force $P_{HDP}$ at the time when the pressure pulse wave detected by the active element of the sensor 46, positioned right above the radial artery 56, detects the greatest one of respective amplitudes $AR_n$ of respective pulses $WR_n$ thereof, and replaces the prior optimum pressing force with the thus determined new optimum pressing force $P_{HDPO}$. Then, the pressing force $P_{HDP}$ applied to the sensor 46 is maintained at the new optimum pressing force $P_{HDPO}$. In the state in which the pressure-pulse-wave sensor 46 is pressed with the new optimum pressing force $P_{HDPO}$, the control device 28 carries out SA5 and the following steps.

At SA5, the control device 28 switches the deflation control valve 16 to its pressure-supply position, and operates the air pump 18, so that the pressure in the cuff 10 is quickly increased for a blood-pressure measurement. At SA6, the control device 28 judges whether the cuff pressure $P_C$ has reached the prescribed first target pressure $P_{CM1}$, i.e., 180 mmHg. If a negative judgment is made at SA6, SA6 is repeated till a positive judgment is made. Thus, the increasing of the cuff pressure $P_C$ is continued.

Meanwhile, if the cuff pressure $P_C$ is increased and a positive judgment is made at SA6, the control goes to SA7 to stop the air pump 18 and switch the deflation control valve 16 to its slow-deflation position, so that the pressure in the cuff 10 is slowly decreased at a prescribed rate of 3 mmHg/sec.

At SA8, the control device 28 reads in the pressure-pulse-wave signal $SM_2$ which is supplied from the active element of the pressure-pulse-wave sensor 46, and the cuff-pressure-pulse signal $SM_1$ which is supplied from the pulse-wave filter circuit 24, each during the slow deflation of the cuff pressure $P_C$. At SA9, the control device 28 judges whether the cuff pressure $P_C$ has decreased down to a prescribed second target pressure $P_{CM2}$, i.e., 60 mmHg. If a negative judgment is made at SA9, SA8 and SA9 are repeated till a positive judgment is made at Step SA9. Thus, while the cuff pressure $P_C$ is slowly decreased, the control device 28 continues reading in the pressure-pulse-wave signal $SM_2$ and the cuff-pressure-pulse signal $SM_1$.

Meanwhile, if a positive judgment is made at SA9, the control goes to SA10 to switch the deflation control valve 16 to its quick-deflation position so that the cuff 10 is quickly deflated. Thus, the signal-obtaining routine is finished. SA5, SA6, SA7, SA9 and SA10 correspond to the cuff-pressure changing means 76.

The signal-obtaining routine is followed by the signal-processing routine shown in FIG. 7. According to the signal-processing routine of FIG. 7, first, the control device 28 carries out SB1 and SB2 corresponding to the average-pressure determining means 84. At SB1, the control device 28 determines a maximal value $P_{Mmax}$ and a minimal value $P_{Mmin}$ of pressure $P_M$ of each of respective heartbeat-synchronous pulses $WR_n$ of the pressure pulse wave read in while SA8 and SA9 of FIG. 6 are repeated. In addition, the control device 28 determines, as a middle pressure $MID_n$, an average of the maximal and minimal values $P_{Mmax}$, $P_{Mmin}$ of each of the respective pulses $WR_n$. At SB2, the control device 28 determines an average $MID_{per}$ of the respective middle pressures $MID_n$ of the respective pulses $WR_n$ determined at SB1.

Then, the control goes to SB3, SB4, and SB5 corresponding to the corrected-cuff-pressure determining means 86. At SB3, the control device 28 subtracts the average pressure $MID_{per}$ determined at SB2, from the middle pressure $MID_n$ of each of the respective pulses $WR_n$, determined at SB1, and thereby determines a pressure difference $\Delta P_n$ for each pulse $WR_n$. Subsequently, at SB4, the control device 28 determines a value $PRS_n$ of the cuff pressure $P_C$ at the time of detection of the amplitude $AK_n$ of one pulse $WK_n$ of the cuff pulse wave that corresponds to the each pulse $WR_n$. Then, at SB5, the control device 28 subtracts the pressure difference $\Delta P_n$ for the each pulse $WR_n$, determined at SB3, from the cuff pressure $PRS_n$ determined at SB4, and thereby determines a corrected cuff pressure $PRS_n'$.

Then, the control goes to SB6 and SB7 corresponding to the average-amplitude determining means 78. At SB6, the control device 28 determines an amplitude ARn as a difference between the maximal and minimal values $P_{Mmax}$, $P_{Mmin}$ of the pressure $P_M$ of each of the pulses $WR_n$ of the pressure pulse wave read in while SA8 and SA9 of FIG. 6 are repeated. At SB7, the control device 28 determines an average $AR_{per}$ of the respective amplitudes $AR_n$ of the respective pulses $WR_n$, determined at SB6.

Subsequently, at SB8 corresponding to the correction-factor determining means 80, the control device 28 determines a correction factor $K_n$ for each pulse $WR_n$, by dividing the average amplitude $AR_{per}$ determined at SB7, by the amplitude $AR_n$ of the each pulse $WR_n$, determined at SB6, according to the previously-indicated expression (1).

Then, at SB9 corresponding to the corrected-cuff-pulse-wave-amplitude determining means 82, the control device 28 multiplies, by the correction factor $K_n$ determined for each pulse $WR_n$ of the pressure pulse wave at SB8, the amplitude $AK_n$ of one of the pulses $WK_n$ of the cuff pulse wave that corresponds to the each pulse $WR_n$, and thereby determines a corrected amplitude $AK_n'$ of the one pulse $WK_n$.

Then, at SB10 corresponding to the blood-pressure determining means 88, the control device 28 determines a systolic blood-pressure value $BP_{SYS}$, a mean blood-pressure value $BP_{MEAN}$, and a diastolic blood-pressure value $BP_{DIA}$ of the patient, based on the change of the respective corrected cuff-pulse-wave amplitudes $AK_n'$ determined at SB9, with respect to the respective corrected cuff-pressure values $PRS_n'$ determined at SB5, according to a well-known oscillometric algorithm. Then, at SB11, the systolic blood-pressure value $BP_{SYS}$, etc. determined at SB10 are displayed on the display device 32. Thus, the present routine is finished.

Figure 9A:
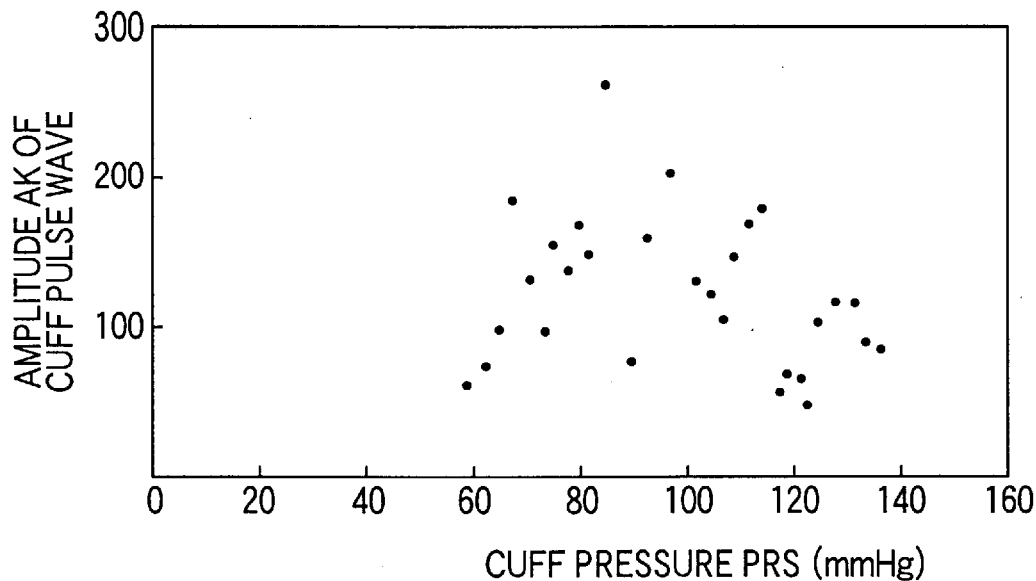
FIG. 9A is a graph obtained by plotting amplitudes $AK_n$ of respective heartbeat-synchronous pulses $WK_n$ of the cuff pulse wave shown in FIG. 8, at corresponding cuff-pressure values $PRS_n$ at respective times of detection of the amplitudes $AK_n$.
Figure 10:
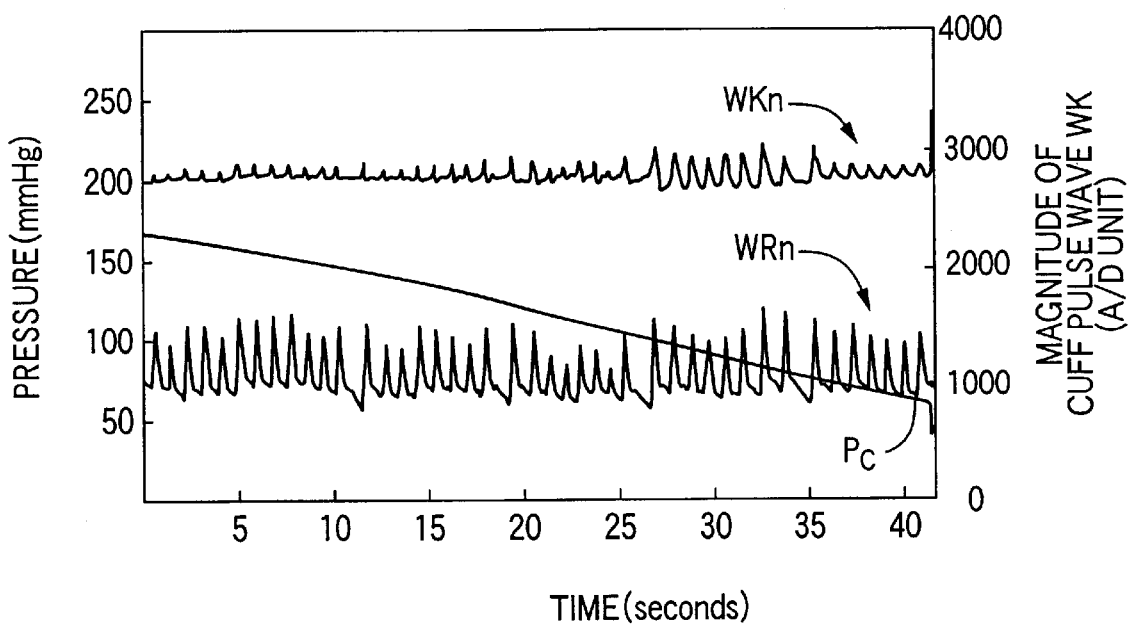
FIG. 10 is a graph showing a cuff pulse wave $WK_n$ and a radial pulse wave $WR_n$ which are obtained, when a cuff pressure $P_C$ is slowly decreased, by the automatic blood-pressure measuring apparatus of FIG. 1 to measure a blood pressure of another patient who suffers arrhythmia.
Figure 11A:
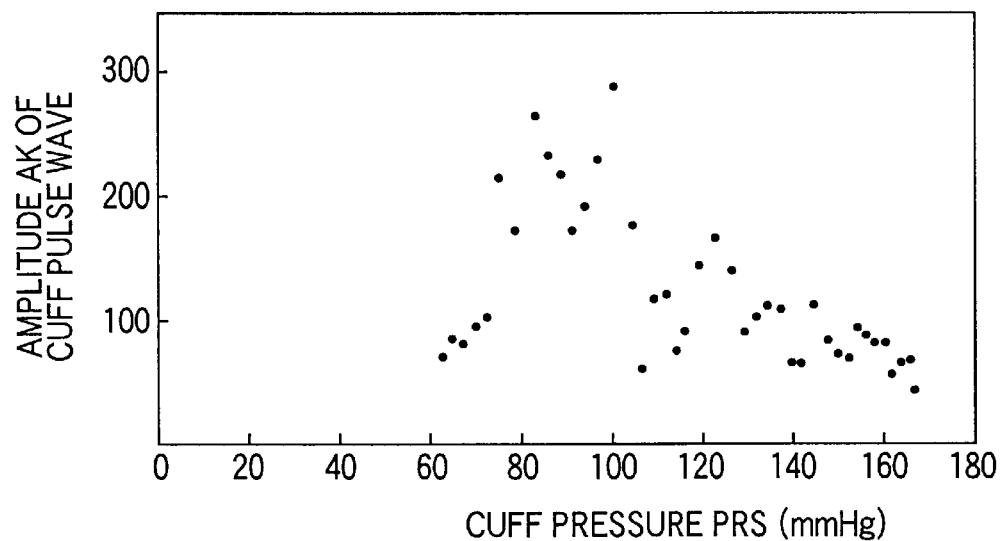
FIG. 11A is a graph obtained by plotting amplitudes $AK_n$ of respective heartbeat-synchronous pulses $WK_n$ of the cuff pulse wave shown in FIG. 10, at corresponding cuff-pressure values $PRS_n$ at respective times of detection of the amplitudes $AK_n$.

Next, there will be described the accuracy of blood pressure values BP measured by the present automatic blood-pressure measuring apparatus 8, by reference to the results obtained from two experiments, shown in FIGS. 8, 9A, 9B, 10, 11A, and 11B. In the two experiments, blood pressure values are measured from two patients who suffer arrhythmia. Each of FIGS. 8 and 10 shows a cuff pulse wave $WK_n$ (expressed in A/D unit) and a radial pulse wave $WR_n$ (expressed in mmHg) which are obtained when the cuff pressure Pc (expressed in mmHg) is slowly decreased. Each of FIGS. 9A and 11A shows a graph obtained by plotting respective amplitudes $AK_n$ of respective pulses $WK_n$ of the cuff pressure wave shown in a corresponding one of FIGS. 8 and 10, at respective cuff-pressure values $PRS_n$ at respective times of detection of the amplitudes $AK_n$. According to the oscillometric method, a systolic blood pressure $BP_{SYS}$ is determined as a cuff pressure PRS at the time of detection of a rising point of an envelope obtained by connecting the plots shown in each of FIGS. 9A and 11A, and a mean blood pressure $BP_{MEAN}$ is determined as a cuff pressure PRS at the time of detection of a peak point of the envelope obtained by connecting the plots shown in each of FIGS. 9A and 11A. That is, a blood pressure BP is determined based on the shape of the envelope. However, the shape of the envelope obtained from each of the two patients who suffer arrhythmia is so unclear as not to allow the determination of accurate blood pressure BP.

Figure 9B:
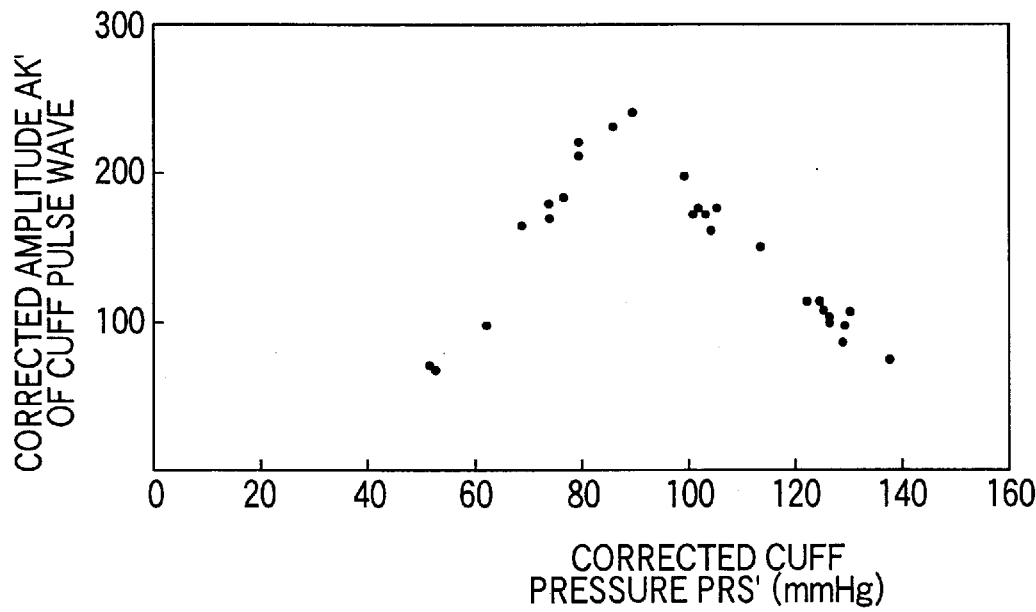
FIG. 9B is a graph showing a relationship between respective corrected cuff-pressure values $PRS_n'$ obtained from the cuff-pressure values $PRS_n$ shown in FIG. 8 and respective corrected cuff-pulse-wave amplitudes $AK_n'$ obtained from the cuff-pulse-wave amplitudes $AK_n$ shown in FIG. 8.
Figure 11B:
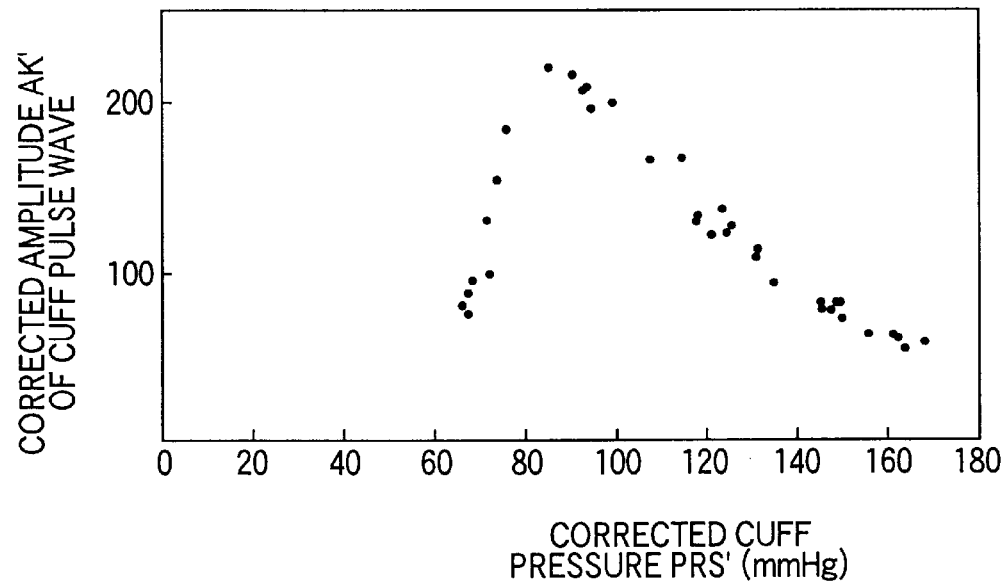
FIG. 11B is a graph showing a relationship between respective corrected cuff-pressure values $PRS_n'$ obtained from the cuff-pressure values $PRS_n$ shown in FIG. 10 and respective corrected cuff-pulse-wave amplitudes $AK_n'$ obtained from the cuff-pulse-wave amplitudes $AK_n$ shown in FIG. 10.

In contrast thereto, each of FIGS. 9B and 11B shows a graph obtained by plotting respective corrected cuff-pulse-wave amplitudes $AK_n'$, obtained from the cuff-pulse-wave amplitudes $AK_n$ shown in a corresponding one of FIGS. 9A and 11A, at respective corrected cuff-pressure values $PRS_n'$ obtained from the cuff-pressure values $PRS_n$ shown in a corresponding one of FIGS. 9A and 11A. Since a clear envelope can be obtained from each of the graphs shown in FIGS. 9B and 11B, an accurate blood pressure BP can be determined.

It emerges from the foregoing description of the illustrated embodiment, that the correction-factor determining means 80 (SB8) determines, for each of the pulses $WR_n$ of the pressure pulse wave continuously detected by the pressure-pulse-wave sensor 46, the correction factor $K_n$ to correct the amplitude $AR_n$ of the each pulse $WR_n$ to the average amplitude $AR_{per}$; and the corrected-cuff-pulse-wave-amplitude determining means 82 (SB9) multiplies, by the correction factor $K_n$ determined for the each pulse $WR_n$, the amplitude $AK_n$ of one of the pulses $WK_n$ of the cuff pulse wave that corresponds to the each pulse $WR_n$, and thereby determines the corrected amplitude $AK_n'$ of the one pulse $WK_n$ that is free of the influence of change of cardiac output during the slow change of the cuff pressure $P_C$. In addition, the average-pressure determining means 84 (SB1 and SB2) determines the average $MID_{per}$ of the respective middle pressures $MID_n$ of the respective pulses $WR_n$ of the pressure pulse wave that are detected during the slow change of the cuff pressure $P_C$; and the corrected-cuff-pressure determining means 86 (SB3, SB4, and SB5) subtracts, from the cuff pressure $PRS_n$ at the time of detection of the amplitude $AK_n$ of one of the pulses $WK_n$ of the cuff pulse wave that corresponds to the each pulse $WR_n$, the pressure difference $\Delta P_n$ obtained by subtracting, from the middle pressure $MID_n$ of the each pulse $WR_n$, the average pressure $MID_{per}$ determined by the average-pressure determining means 84 (SB1 and SB2), and thereby determines the corrected cuff pressure $PRS_n'$ that indicates a cuff pressure $P_C$ which would be detected, at the time of detection of the amplitude $AK_n$ of the one pulse $RK_n$ of the cuff pulse wave, in the state in which there would be no influence of change of blood pressure of the subject. And, the blood-pressure determining means 88 (SB10) determines the blood pressure BP of the subject based on the change of the respective corrected cuff-pulse-wave amplitudes $AK_n'$ determined by the corrected-cuff-pulse-wave-amplitude determining means 82 (SB9) with respect to the respective corrected cuff-pressure values $PRS_n'$ determined by the corrected-cuff-pressure determining means 86 (SB3, SB4, and SB5). Thus, the present apparatus 8 can determine the blood pressure BP with high accuracy.

While the present invention has been described in its preferred embodiment by reference to the drawings, it is to be understood that the invention may otherwise be embodied.

For example, in the illustrated embodiment, the middle pressure $MID_n$ of each pulse $WR_n$ of the pressure pulse wave is used as the reference pressure of the each pulse $WR_n$, and the average $MID_{per}$ of the respective middle pressures $MID_n$ of the pulses $WR_n$ is used as the average pressure of the respective reference pressures of the pulses $WR_n$. However, the reference pressure of each pulse $WR_n$ may be any pressure that can be determined based on the waveform of the each pulse $WR_n$. Therefore, in place of the middle pressure $MID_n$, it is possible to employ, as the reference pressure, a maximal pressure (i.e., a maximal pulse pressure) $P_{Mmax}$ of each pulse $WR_n$, a pressure corresponding to a center of gravity of an area defined by the waveform of each pulse $WR_n$, or a pressure equal to the sum of a minimal pressure $P_{Mmin}$ of each pulse $WR_n$ and one third of an amplitude $AR_n$ of the each pulse $WR_n$.

In the illustrated embodiment, the average-amplitude determining means 78 determines the average $AR_{per}$ of the respective amplitudes $AR_n$ of the respective pulses $WR_n$ of the pressure pulse wave detected during the slow change of the cuff pressure $P_C$; and the correction-factor determining means 80 determines, by dividing the average amplitude ARper by the amplitude $AR_n$ of each of the pulses $WR_n$ according to the expression (1), the correction factor $K_n$ to correct the amplitude $AR_n$ of the each pulse $WR_n$ to the average amplitude $AR_{per}$ (i.e., a predetermined value). However, the correction factors $K_n$ may be any values that correct the respective amplitudes $AR_n$ of the pulses $WR_n$ each to a predetermined value. Therefore, in the expression (1), the average amplitude $AR_{per}$ may be replaced with, e.g., a prescribed standard value, or an amplitude $AR_1$ of a first pulse $WR_1$ of the pressure pulse wave that is first detected by the active element of the pressure-pulse-wave sensor 46 during the slow deflation of the cuff pressure $P_C$.

In the illustrated embodiment, the cuff-pressure changing means 76 (SA7 and SA9) slowly decreases the cuff pressure $P_C$ down to the prescribed second target pressure $P_{CM2}$. However, the average-amplitude determining means 78 (SB6 and SB7), the correction-factor determining means 80 (SB8), the corrected-cuff-pulse-wave-amplitude determining means 82 (SB9), the average-pressure determining means 84 (SB1 and SB2), the corrected-cuff-pressure determining means 86 (SB3, SB4, SB5), and the blood-pressure determining means 88 (SB10) may be modified such that during the slow deflation of the cuff pressure $P_C$, those means 78, 80, 82, 84, 86, 88 iteratively operate at respective times to process respective lengths of the cuff-pulse-wave signal $SM_1$ and the pressure-pulse-wave signal $SM_2$ that have been read in up to each of those times. In the latter case, the slow deflation of the cuff pressure $P_C$ may be stopped upon determination of the diastolic blood pressure $BP_{DIA}$.

In the illustrated embodiment, both the cuff-pressure values $PRS_n$ and the cuff-pulse-wave amplitudes $AK_n$ are corrected to the corrected cuff-pressure values $PRS_n'$ and the cuff-pulse-wave amplitudes $AK_n'$, respectively, based on which the blood pressure BP is determined. However, it is possible to correct either the cuff-pressure values $PRS_n$ or the cuff-pulse-wave amplitudes $AK_n$ to the corrected cuff-pressure values $PRS_n'$ or the corrected cuff-pulse-wave amplitudes $AK_n'$, because a blood pressure BP determined based on the cuff-pressure values $PRS_n$ or the cuff-pulse-wave amplitudes $AK_n$, and the corrected cuff-pulse-wave amplitudes $AK_n'$ or the corrected cuff-pressure values $PRS_n'$ is freed, to some degree, of the influence of change of blood pressure of the subject during the blood-pressure measuring operation.

It is to be understood that the present invention may be embodied with other changes, improvements, and modifications that may occur to a person skilled in the art without departing from the spirit and scope of the invention defined in the appended claims.

What is claimed is:

1. An apparatus for automatically measuring a blood pressure of a living subject, comprising:

an inflatable cuff which is adapted to be wound around a portion of the subject, a cuff pulse wave including a plurality of heartbeat-synchronous pulses occurring to the cuff when a pressure in the cuff is changed;

a pressure-pulse-wave detecting device which includes a pressure-pulse-wave sensor that is adapted to be pressed against an artery of the subject and which detects, through the pressure-pulse-wave sensor, a pressure pulse wave that is produced by the artery when the pressure of the cuff is changed and that includes a plurality of heartbeat-synchronous pulses;

an average-pressure determining means for determining an average pressure of respective reference pressures of the heartbeat-synchronous pulses of the pressure pulse wave that are detected by the pressure-pulse-wave detecting device when the pressure of the cuff is changed;

a corrected-cuff-pressure determining means for subtracting, from a pressure of the cuff at a time of detection of one of the heartbeat-synchronous pulses of the cuff pulse wave that corresponds to each of the heartbeat-synchronous pulses of the pressure pulse wave, a pressure difference obtained by subtracting, from the reference pressure of said each heartbeat-synchronous pulse of the pressure pulse wave, the average pressure determined by the average-pressure determining means, and thereby determining a corrected pressure of the cuff; and a blood-pressure determining means for determining a blood pressure of the subject based on a change of respective amplitudes of the respective heartbeat-synchronous pulses of the cuff pulse wave, with respect to the respective corrected pressures of the cuff.

2. An apparatus according to claim 1, wherein the average-pressure determining means comprises means for determining the average pressure of respective middle pressures of the heartbeat-synchronous pulses of the pressure pulse wave that are detected by the pressure-pulse-wave detecting device when the pressure of the cuff is changed, and wherein the corrected-cuff-pressure determining means comprises means for subtracting, from the pressure of the cuff at the time of detection of said one of the heartbeat-synchronous pulses of the cuff pulse wave that corresponds to said each of the heartbeat-synchronous pulses of the pressure pulse wave, the pressure difference obtained by subtracting, from the middle pressure of said each heartbeat-synchronous pulse of the pressure pulse wave, the average pressure determined by the average-pressure determining means, and thereby determining the corrected pressure of the cuff.

3. An apparatus for automatically measuring a blood pressure of a living subject, comprising:

an inflatable cuff which is adapted to be wound around a portion of the subject and which is connected to a pressure sensor for detecting a cuff pulse wave including a plurality of heartbeat-synchronous pulses occurring to the cuff when a pressure in the cuff is changed;

a pressure-pulse-wave detecting device which includes a pressure-pulse-wave sensor that is adapted to be pressed against an artery of the subject which is other than the downstream from the cuff and which detects, through the pressure-pulse-wave sensor, a pressure pulse wave that is produced by the artery when the pressure of the cuff is changed and that includes a plurality of heartbeat-synchronous pulses;

a correction-factor determining means for determining, for each of the heartbeat-synchronous pulses of the pressure pulse wave, a correction factor to correct an amplitude of said each heartbeat-synchronous pulse to a predetermined value;

a corrected-cuff-pulse-wave-amplitude determining means for multiplying, by the correction factor determined by the correction-factor determining means for said each of the heartbeat-synchronous pulses of the pressure pulse wave, an amplitude of one of the heartbeat-synchronous pulses of the cuff pulse wave that corresponds to said each heartbeat-synchronous pulse of the pressure pulse wave, and thereby determining a corrected amplitude of said one heartbeat-synchronous pulse of the cuff pulse wave; and a blood-pressure determining means for determining a blood pressure of the subject according to the oscillometric method based on a change of the respective corrected amplitudes of the respective heartbeat-synchronous pulses of the cuff pulse wave, with respect to the pressure of the cuff.

4. An apparatus according to claim 3, further comprising:

a pressure changing device which changes the pressure of the cuff;

a pressure sensor which detects the pressure of the cuff changed by the pressure changing device; and a cuff-pulse-wave detecting device which detects the cuff pulse wave occurring to the cuff.

5. An apparatus according to claim 3, wherein the correction-factor determining means comprises:

means for determining an average amplitude of respective amplitudes of the heartbeat-synchronous pulses of the pressure pulse wave; and means for determining, for said each of the heartbeat-synchronous pulses of the pressure pulse wave, the correction factor to correct the amplitude of said each heartbeat-synchronous pulse to the determined average amplitude as the predetermined value.

6. An apparatus for automatically measuring a blood pressure of a living subject, comprising:

an inflatable cuff which is adapted to be wound around a portion of the subject, a cuff pulse wave including a plurality of heartbeat-synchronous pulses occurring to the cuff when a pressure in the cuff is changed;

a pressure-pulse-wave detecting device which includes a pressure-pulse-wave sensor that is adapted to be pressed against an artery of the subject and which detects, through the pressure-pulse-wave sensor, a pressure pulse wave that is produced by the artery when the pressure of the cuff is changed and that includes a plurality of heartbeat-synchronous pulses;

a correction-factor determining means for determining, for each of the heartbeat-synchronous pulses of the pressure pulse wave, a correction factor to correct an amplitude of said each heartbeat-synchronous pulse to a predetermined value;

a corrected-cuff-pulse-wave-amplitude determining means for multiplying, by the correction factor determined by the correction-factor determining means for said each of the heartbeat-synchronous pulses of the pressure pulse wave, an amplitude of one of the heartbeat-synchronous pulses of the cuff pulse wave that corresponds to said each heartbeat-synchronous pulse of the pressure pulse wave;

an average-pressure determining means for determining an average pressure of respective reference pressures of the heartbeat-synchronous pulses of the pressure pulse wave that are detected by the pressure-pulse-wave detecting device when the pressure of the cuff is changed;

a corrected-cuff-pressure determining means for subtracting, from a pressure of the cuff at a time of detection of said one of the heartbeat-synchronous pulses of the cuff pulse wave that corresponds to said each of the heartbeat-synchronous pulses of the pressure pulse wave, a pressure difference obtained by subtracting, from the reference pressure of said each heartbeat-synchronous pulse of the pressure pulse wave, the average pressure determined by the average-pressure determining means; and a blood-pressure determining means for determining a blood pressure of the subject based on a change of the respective corrected amplitudes of the respective heartbeat-synchronous pulses of the cuff pulse wave, with respect to the respective corrected pressures of the cuff.

7. An apparatus for automatically measuring a blood pressure of a living subject, comprising:

an inflatable cuff which is adapted to be wound around a portion of the subject, a cuff pulse wave including a plurality of heartbeat-synchronous pulses occurring to the cuff when a pressure in the cuff is changed;

a pressure-pulse-wave detecting device which includes a pressure-pulse-wave sensor that is adapted to be pressed against an artery of the subject and which detects, through the pressure-pulse-wave sensor, a pressure pulse wave that is produced by the artery when the pressure of the cuff is changed and that includes a plurality of heartbeat synchronous pulses;

a correction-factor determining means for determining, for each of the heartbeat-synchronous pulses of the pressure pulse wave, a correction factor to correct an amplitude of said each heartbeat-synchronous pulse to a predetermined value;

a corrected-cuff-pulse-wave-amplitude determining means for multiplying, by the correction factor determined by the correction-factor determining means for said each of the heartbeat-synchronous pulses of the pressure pulse wave, an amplitude of one of the heartbeat-synchronous pulses of the cuff pulse wave that corresponds to said each heartbeat-synchronous pulse of the pressure pulse wave, and thereby determining a corrected amplitude of said one heartbeat-synchronous pulse of the cuff pulse wave; and a blood-pressure determining means for determining a blood pressure of the subject based on a change of the respective corrected amplitudes of the respective heartbeat-synchronous pulses of the cuff pulse wave, with respect to the pressure of the cuff;

wherein the correction-factor determining means comprises:

means for determining an average amplitude of respective amplitudes of the heartbeat-synchronous pulses of the pressure pulse wave; and means for determining, for said each of the heartbeat-synchronous pulses of the pressure pulse wave, the correction factor to correct the amplitude of said each heartbeat-synchronous pulse to the determined average amplitude as the predetermined value.

* * * * *